United States Patent [19]

Sakurai

[11] Patent Number: 5,533,398
[45] Date of Patent: Jul. 9, 1996

[54] METHOD AND APPARATUS FOR TESTING LEAD CONNECTIONS OF ELECTRONIC COMPONENTS

[75] Inventor: Keizoh Sakurai, Shiga-ken, Japan

[73] Assignee: International Business Machines Corporation, Armonk, N.Y.

[21] Appl. No.: 241,903

[22] Filed: May 12, 1994

[30] Foreign Application Priority Data

May 13, 1993 [JP] Japan ................................ 5-111304

[51] Int. Cl.$^6$ .......................... G01M 7/00; G01N 3/48; G01N 3/32
[52] U.S. Cl. ................................ 73/573; 73/815
[58] Field of Search .................. 73/842, 841, 815, 73/778, 862.01, 862.59, 588

[56] References Cited

U.S. PATENT DOCUMENTS

| | | | |
|---|---|---|---|
| 3,153,338 | 10/1964 | Kleesattel | 73/815 |
| 3,958,450 | 5/1976 | Kleesattel | 73/573 |
| 4,040,885 | 8/1977 | Hight et al. | 73/588 |
| 4,218,922 | 8/1980 | Ensminger | 73/588 |
| 4,232,558 | 11/1980 | Jon et al. | 73/801 |
| 4,763,409 | 8/1988 | Takekawa et al. | 29/827 |
| 4,854,494 | 8/1989 | von Raben | 73/588 |
| 5,170,929 | 12/1992 | Long et al. | 228/102 |

FOREIGN PATENT DOCUMENTS 3-63562  3/1991  Japan ........................ 73/850

OTHER PUBLICATIONS

Kuhns, L., "Nondestructive Testing of Lead Bonds", Jan. 1974, Western Electric Technical Digest No. 33, p. 35.
Western Electric Technical Digest, No. 33, p. 35, Jan., 1974, "Nondestructive testing of lead bonds", by Kuhns.

Primary Examiner—Richard Chilcot
Assistant Examiner—William L. Oen
Attorney, Agent, or Firm—Michael E. Belk

[57] ABSTRACT

To test the quality of solder bonded lead connections of a package by applying a shearing force to the leads using ultrasonic vibration and by measuring the resultant strain. A probe 32 is pressed against the surface of a lead 12 and vibrated by a piezoelectric element 38 in parallel with the lead surface to apply a shearing force to the solder bond portion. The resultant strain occurring in the solder bond portion is correlated with current and impedance of the piezoelectric element 38. By measuring the current and/or impedance of the piezoelectric element, the quality of the solder bond portion can be determined. Thus, a circuit board is produced having solder joints whose maximum strain in reaction to load is limited by the amount exhibited by a good joint.

22 Claims, 4 Drawing Sheets

METHOD AND APPARATUS FOR TESTING LEAD CONNECTIONS OF ELECTRONIC COMPONENTS

FIELD OF THE INVENTION

The present invention relates to a method and apparatus for testing circuit boards or cards. In the field of circuit board assembly, electronic components have leads which are connected to the boards. More specifically, the invention relates to a method and apparatus for testing, at high speed and with high reliability, lead connections of semiconductor chip packages that are bonded to substrates with solder.

BACKGROUND

In general, a semiconductor chip package or module having leads is connected to a chip carrier substrate by a bonding material such as solder. Various lead connection testing methods have been proposed, including an optical testing method using a camera, an X-ray testing method, and an electric testing method in which a conduction test is performed. However, the detection accuracy of these testing methods is limited. For example, as shown in FIG. 9, solder joints or bond portions 14, which connects leads 12 of a chip package 10 to conductors 16 of a chip carrier substrate 18 such as a printed circuit board or a ceramic substrate, may include a crack 24 or foreign matter 26. Since the connection strength of such a lead is essentially low even though it may have a good appearance, after shipment of a product it may peel off from the substrate due to some external force or the like, causing an open circuit fault. Recently, the number of leads per chip has greatly increased, and the solder amount per lead has been reduced accordingly. Therefore, inclusion of even a small crack or scratch or a small foreign body may break the connection, causing a conduction fault or an open circuit fault. However, the optical testing method, X-ray testing method and electric testing method cannot find all such minute defects within solder joints, which are potential causes of conduction faults.

Japanese Published Examined Patent Application No. 61-7016 discloses a technique of testing the quality of lead connections by applying a vertical vibration to a selected point of a lead from a vibrator probe and detecting resulting variation in the probe vibration with a piezoelectric pickup. Although this method can detect a connection defect of a kind which cannot be detected by the optical testing method and so on, it has the problem of slow detection speed. More specifically, even a lead connection with the defect of insufficient solder may be detected as a good connection if solder happens to exist at the point of probe landing. To avoid this problem, it is necessary to use a plurality of testing points for each lead, in which case the probe is moved to a plurality of testing points and the testing procedure is repeated for each of the testing points. Therefore, if there are a large number of leads, the testing speed is very slow. In the method of this patent, the connection quality is judged by analyzing the vibration detected by the piezoelectric pickup, probe tapping sound detected by a microphone, or lead surface displacement detected optically.

Japanese Published Unexamined Patent Application No. 2-54169 discloses a technique of testing connection quality by contacting a vibration finger with a lead of an IC package and detecting the vibration of the lead with a pickup. In this method, the vibration frequency of the finger is changed, and the frequency-vibration characteristic of the lead is detected. The vibration finger is inserted into a gap between adjacent leads at a position close to the package, and brought in contact with the side of the lead. Since the vibration is applied to the lead at the position away from the actual solder joint, there exists a problem of a small difference between signals associated with good and defective connections, i.e., a low defect discrimination ability. Further, since the finger needs to be inserted into a gap between the leads, this method cannot be applied to a high-density package with a small lead pitch. In the method of this patent publication, the connection quality is judged by comparing the frequency-vibration characteristics of the pickup output with reference characteristics, which requires complex processing.

OBJECTS OF THE INVENTION

An object of the present invention is to provide a method and apparatus for testing soldered lead connections of an electronic component in a simple manner, at high speed, and with high reliability, which method and apparatus can be applied to the testing of a high-density electronic component with a small lead pitch.

SUMMARY OF THE INVENTION

In a testing method according to the present invention, the tip of a probe is pressed onto the surface of a lead connected to a substrate by a joint such as solder which can cause strain when subjected to a shearing force, and the probe is vibrated in parallel with the lead surface. The strain caused in the joint by the vibration is detected, and the quality of the lead connection is judged based on the detected strain. The vibration of the probe is generated by a piezoelectric element, and the quality judgment is performed based on current or impedance of the piezoelectric element.

A testing apparatus according to the invention includes a probe assembly which includes a probe and a piezoelectric element for vibrating the probe in a direction perpendicular to the axis of the probe; means for positioning the probe assembly so that the tip of the probe is placed on the surface of the lead; means for applying a predetermined load to the probe so that the tip of the probe is pressed against the surface of the lead; means for energizing the piezoelectric element; means for detecting a strain caused in the joint by the vibration of the probe; and means for judging the quality of the lead connection based on the detected strain. The strain detecting means includes means for measuring current or impedance of the piezoelectric element.

When the probe is vibrated by the piezoelectric element in parallel with the lead surface with the probe pressed against the lead, the probe imparts a shearing force to the joint by frictional engagement to cause, in the joint, a strain that corresponds to its connection strength. The vibration of the probe varies correspondingly to the magnitude of the strain, and the variation in the probe vibration in turn causes a corresponding variation in the current and, therefore, the impedance of the piezoelectric element. Therefore, the strain and the corresponding connection strength can be determined based on the current or impedance of the piezoelectric element, and the lead connection quality can be judged.

BRIEF DESCRIPTION OF THE DRAWINGS

FIG. 5A–5D shows strain deformations of solder joints;

DESCRIPTION OF SYMBOLS

Figure 1:
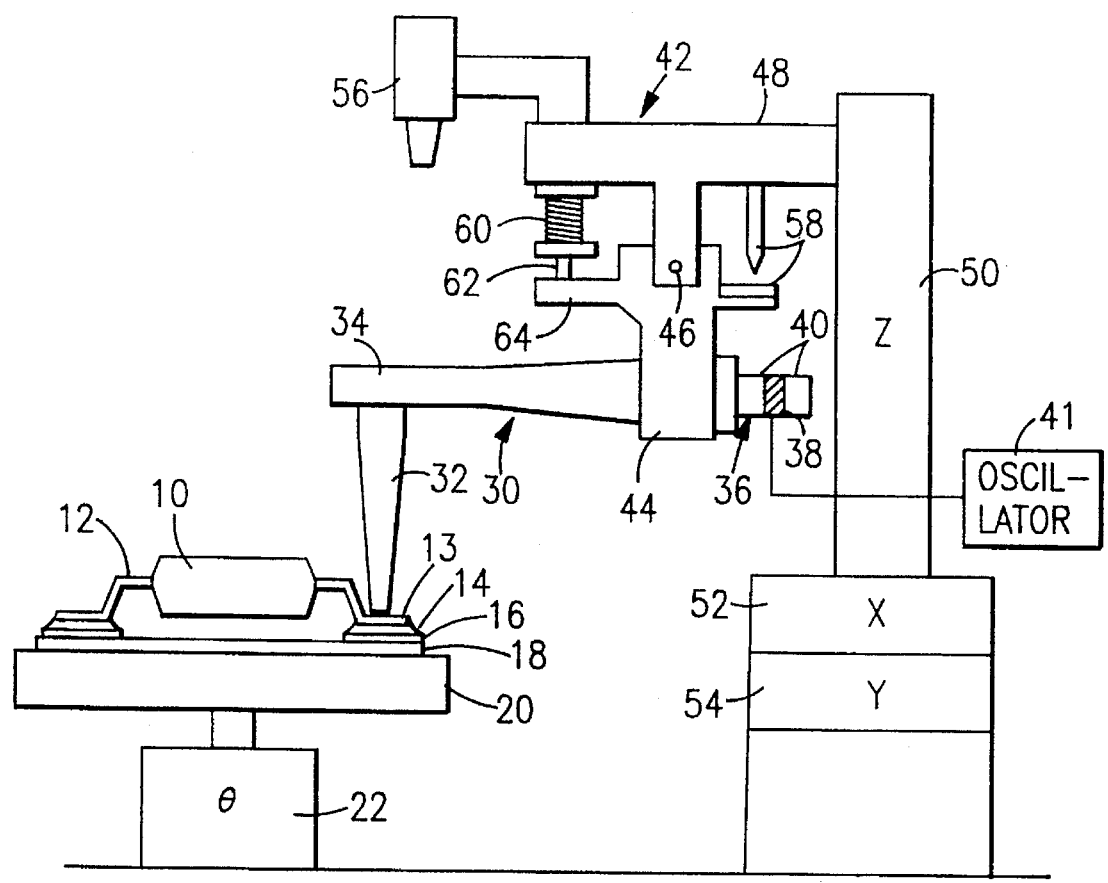
FIG. 1 shows a testing apparatus according to the present invention.

10 . . . Chip package
12 . . . Lead
13 . . . Lead portion to be connected
14 . . . Solder
16 . . . Conductor
18 . . . Substrate
20 . . . Test stage
22 . . . Rotary drive unit
30 . . . Probe assembly
31 . . . Probe vibrating direction
32 . . . Probe
34 . . . Horn
36 . . . Vibrator
38 . . . Piezoelectric element
40 . . . Holding member
41 . . . Oscillator
42 . . . Test head
44 . . . Horn supporting member
50 . . . Z-axis drive unit
52 . . . X-axis drive unit
54 . . . Y-axis drive unit
56 . . . Camera
58 . . . Contact sensor
60 . . . Load coil
62 . . . Rod
64 . . . Protrusion
74 . . . Rectifier circuit
75 . . . Sampling circuit
76 . . . A/D conversion circuit
78 . . . Control unit
80 . . . Storage unit

DETAILED DESCRIPTION OF THE DRAWINGS

A preferred embodiment is now described with reference to the drawings. It is to be noted that the respective drawings are simplified, and not accurately scaled.

FIG. 1 is a schematic view of a lead connection testing apparatus according to the present invention. A chip package 10 to be tested is mounted on a chip carrier substrate 18 such as a printed circuit board or a ceramic substrate. The package 10 has leads 12 of so-called gull-wing type, and their end portions 13 are connected to conductors 16 of the substrate 18 by solder 14 as a bonding material. The substrate 18 is placed on a test stage 20, which is connected to a rotary drive unit 22.

A probe assembly 30 consisting of a test probe 32, a horn 34 and a vibrator 36 is supported by a horn supporting member 44 of a test head 42. This type of probe assembly 30 is well known. The vibrator 36 is constituted of aluminum holding members 40 and a piezoelectric element 38 that is connected to an oscillator 41. The mechanical vibration generated by the vibrator 36 includes not only a main frequency component which is equal to the oscillation frequency of the oscillator 41 but also noise components of other frequencies. The horn 34 is made of a stainless-type metal, and resonates at the frequency of the oscillator 41 to thereby attenuate the other frequency components. The probe 32 is so constructed as to resonate with the mechanical vibration transmitted by the horn 34. The probe assembly 30 will be described later.

The probe holding member 44 is supported by an arm 48 so as to be able to pivot about an axis 46. The arm 48 is connected to a Z-axis drive unit 50 for positioning in the Z-direction. The testing apparatus also has an X-axis drive unit 52 and a Y-axis drive unit 54 for positioning in the X-direction and the Y-direction, respectively. A camera 56 is mounted on the arm 48.

The testing operation is performed in the following manner. When the lead position is detected by the camera 56, the probe 32 is moved by the rotary drive unit 22, Z-axis drive unit 50, X-axis drive unit 52 and Y-axis drive unit 54 to be positioned over the connecting portion 13 of the lead 12. Then the probe 32 is lowered. When the probe 32 is brought into contact with the lead end portion 13 and the arm 48 continues to move downward, the horn support member 44 rotates clockwise about the axis 46 to open contacts of a contact sensor 58. As a result, the arm 48 stops the downward movement and a load coil 60 operates to drive a rod 62 downward. The rod 62 engages with a protrusion 64 of the horn support member 44 to drive the horn support member 44 counterclockwise. As a result, a predetermined vertical load is given to the probe 32. In this state, the piezoelectric element 38 is energized by the oscillator 41. The probe 32 vibrates and the solder joint 14 is tested as described below. When the solder joint 14 has been tested, the probe 32 is elevated and positioned at the next lead 12, and the same procedure is repeated.

Figure 2:
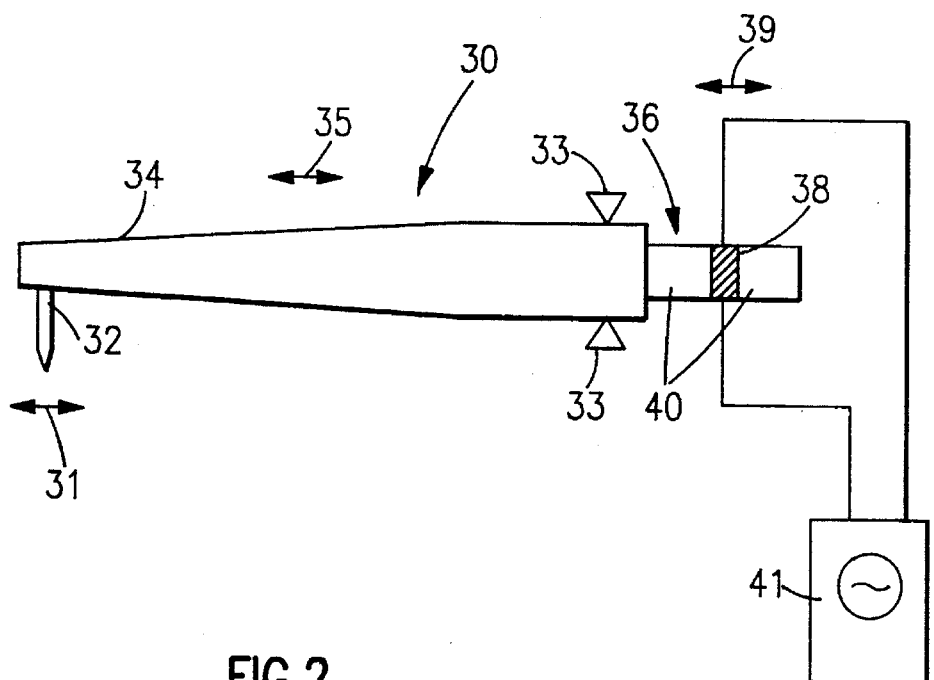
FIG. 2 shows a probe assembly used in the invention.
Figure 3:
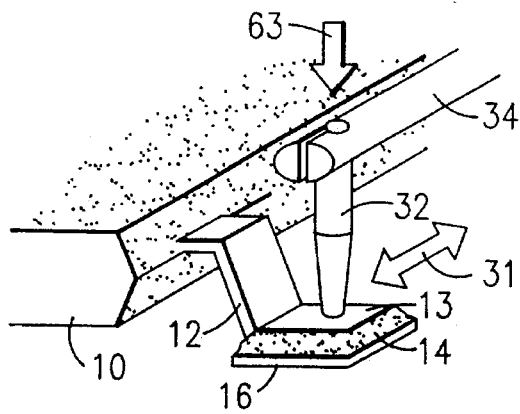
FIG. 3 is a partial view showing a state of a probe being placed on a lead.

Next, the generation of the vibration and the principle of the testing by the probe assembly 30 are described. FIG. 2 shows the probe assembly 30, and FIG. 3 shows the state in which the probe 32 is in contact with the connecting portion 13 of the lead 12 of the chip package 10. Connected to the oscillator 41, the piezoelectric element 38 vibrates longitudinally (arrow 39) in response to the oscillation signal sent from the oscillator 41. The horn 34 vibrates longitudinally (arrow 35) at the desired frequency, and the probe 32 vibrates laterally (arrow 31), i.e., in the direction perpendicular to its axis. The horn support member 44 (see FIG. 1) supports the horn 34 at a node 33 of the horn vibration so as not to affect the resonance state of the horn 34. The probe 32 is attached to the horn 34 at an antinode of the horn vibration.

The probe 32 may be made of ceramic material or a suitable metal. As is understood from FIG. 3, the probe 32 is tapered and its tip is made flat. Preferably, the probe 32 is disposed perpendicularly to the lead 12, and forced to vibrate laterally in parallel with the surface of the lead end portion 13 while receiving a load 63. In FIG. 3, the probe 32 is forced to vibrate in the width direction of the lead 12 (indicated by arrow 31). The purpose of the lateral vibration of the probe 32 is to apply a shearing force to the solder joint or bond portion 14 thereby to cause a shearing strain therein. In general, since the solder joint 14 is smaller in the width direction of the lead 12 than in its longitudinal direction, the strain can be generated more easily in the width direction than in the longitudinal direction. However, the probe 32 may also be vibrated in the longitudinal direction or in an oblique direction.

Figures 4A, 4B:
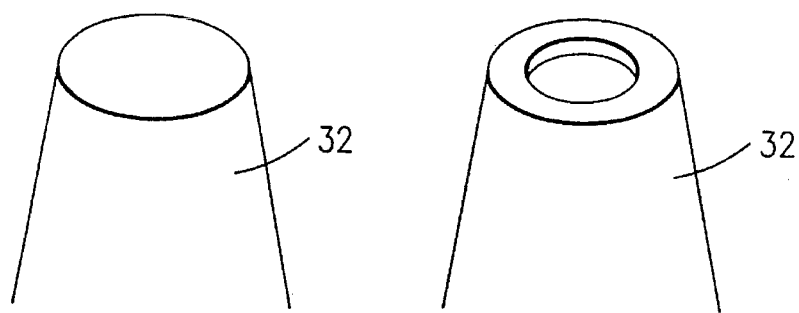
FIG. 4A–4D shows tips of probes.
Figures 4C, 4D:
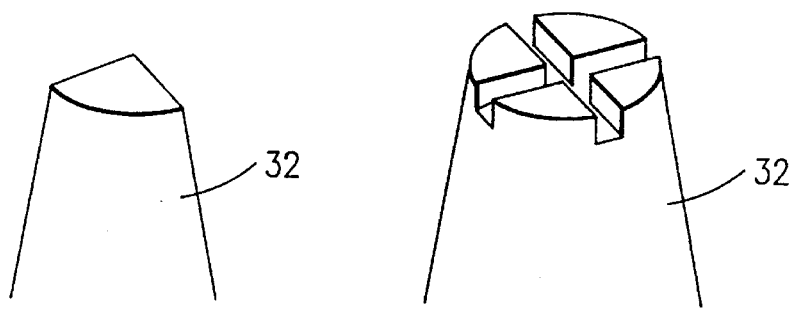

The shearing force imparted to the solder 14 correlates with the product of the vertical load 63 and a friction coefficient between the probe 32 and the lead electrode surface. Therefore, a controlled shearing force can be applied to the solder 14 through the probe vibration by controlling the vertical load 63 and the friction coefficient. The friction coefficient depends on the tip shape of the probe 32, which is exemplified in FIG. 4. Part (A) of FIG. 4 shows a circular, flat tip shape; part (B) shows a shape in which a circular hole is formed in the tip of part (A); part (C) shows a shape having a quadrant tip surface; and part (D) shows a shape in which a cruciform groove is formed in the tip of part (A). It is noted that the face of the tip of the probe 32 is not limited to the above shapes but may take any suitable shape.

Figure 5A:
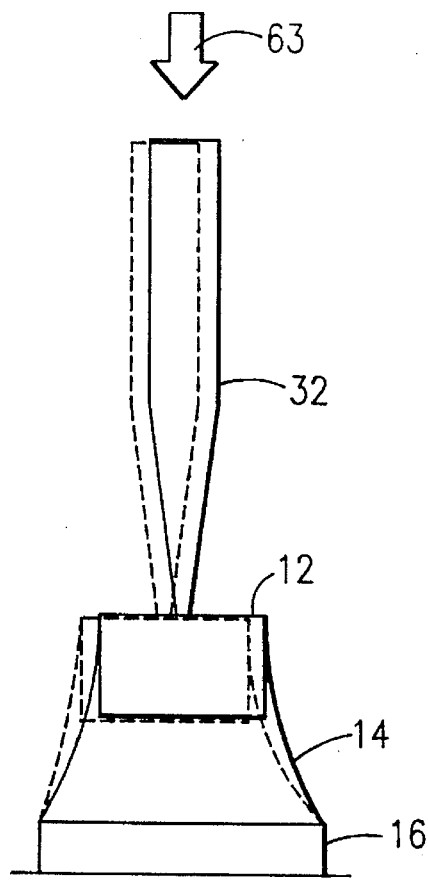
Figure 5B:
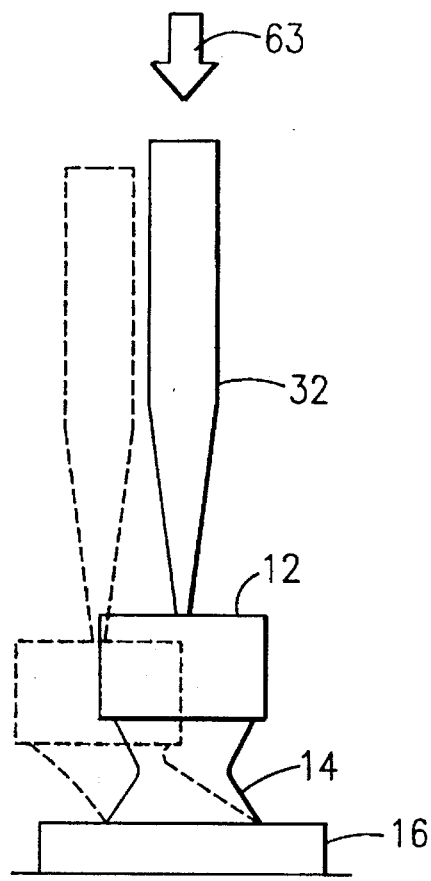
Figure 9:
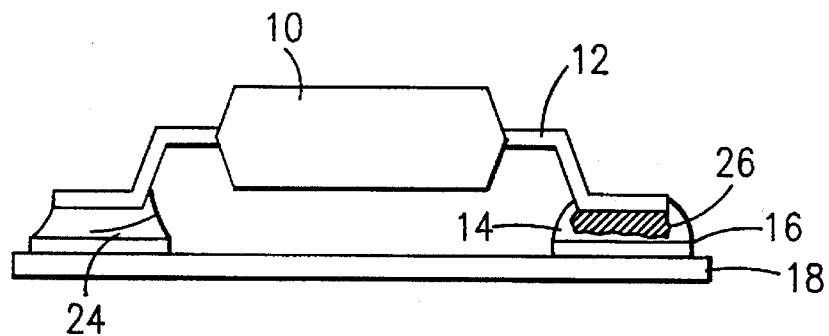
FIG. 9 shows examples of defects of package lead connection.

FIG. 5 shows shearing strain or deformation generated in the solder 14 by leftward movement of the probe 32. The strain generated in the solder joint 14 in response to the shearing force that is applied thereto from the probe 32 depends on the connection strength of the solder joint 14. Part (A) of FIG. 5 shows a case in which the solder joint 14 is in a good connection state and the strain is small. Part (B) of FIG. 5 shows a case in which the solder amount is insufficient and the strain is large. The solid lines indicate the state before the deformation, and the dashed lines indicate the state after the deformation. In actual operation, the probe 32 vibrates in the right-left direction and the solder joint 14 deforms accordingly.

Therefore, it is possible to determine the connection strength of the solder joint 14 and thus its quality based on the amount of the strain when the shearing force is applied to the solder joint 14 through the probe 32. The vibration amplitude of the probe tip when a constant AC signal is applied to the piezoelectric element 38 is large under the unloaded condition in which the probe tip is not in contact with the lead 12, and is small, due to the frictional engagement, under the loaded condition in which the probe tip is in contact with the lead 12. The strain or deformation of the solder 14 is smaller than the vibration amplitude of the probe tip under the loaded or landed condition. Therefore, it is possible to make a judgment of the connection strength of the solder joint 14 without damaging a good solder joint, i.e., in a nondestructive manner, by setting the electric power supplied to the piezoelectric element 38 and the vertical load so that the vibration amplitude of the probe tip in the landed state is within the elastic limit.

Experiments have shown that when a constant AC signal is applied to the piezoelectric element 38, there is a correlation between the vibration amplitude of the probe tip and the current flowing through the piezoelectric element 38. This is explained as follows. When the probe 32 is in the unloaded state and the piezoelectric element 38 expands and contracts freely without any mechanical restraint, the electric resistance and thus impedance of the piezoelectric element 38 when it is regarded as an electrical part, is small. On the other hand, when the probe 32 is in the landed state and the probe vibration is mechanically restrained, the expansion/contraction of the piezoelectric element 38 is also hindered, in which case the impedance of the piezoelectric element 38 increases essentially in proportion to the mechanical restraining force. The mechanical restraining force to the vibration of the piezoelectric element 38 is substantially proportional to the connection strength of the solder joint 14 and substantially inversely proportional to the vibration amplitude of the probe tip and the strain. Thus, it has been found that the strain in the solder joint 14 is substantially inversely proportional to the connection strength and the impedance of the piezoelectric element 38.

Experiments have shown that the estimated breaking strength of the solder joint 14 and the impedance of the piezoelectric element 38 have a relationship that can be approximated by the following linear equation:
(Equation 1)
(Estimated Breaking Strength)=a×(Impedance of Piezoelectric Element)+b
where a and b are constants and can be determined by experiment. The constants a and b vary depending on the test conditions such as the vertical load and the oscillator voltage, and the constant a may be a value on the order of 2 and the constant b may be on the order of 40 to 50. Therefore, the breaking strength and the corresponding strain can be obtained from the impedance of the piezoelectric element 38.

If the frequency of the oscillation signal applied to the piezoelectric element 38 exceeds about 10 kHz, the probe tip may slip on the lead surface. While the slippage can be controlled to a large extent by properly selecting the friction coefficient and the vertical load to the probe 32, it has been found that this has no substantial influence on the measurement result based on Equation (1).

Figure 6:
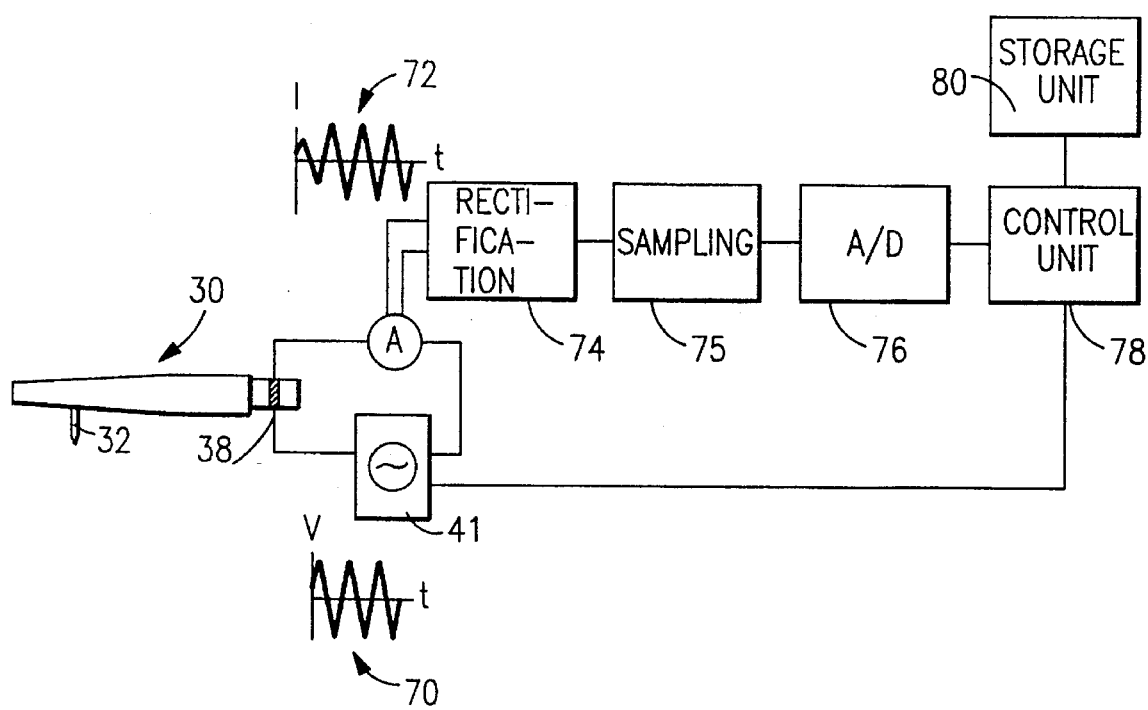
FIG. 6 is a block diagram showing the constitution of a detection circuit of the invention.

Next, a description is made of a method for quick determination of impedance of the piezoelectric element 38 according to the invention. FIG. 6 shows the constitution of a testing circuit of the invention. When the test is started, a control unit 78 such as a processor turns on the oscillator 41 for a predetermined period. The piezoelectric element 38 is energized by a sinusoidal signal 70 sent from the oscillator 41, and a current 72 flowing through the piezoelectric element is rectified by a rectifier circuit 74. The rectified current is sampled about 50 times by a sampling circuit 75, and then digitized by an A/D conversion circuit 76. The control unit 78 calculates an averaged impedance according to the following equation:
(Equation 2)
Z=(Number of Sampling Times)×(Effective Value of Oscillator Output Voltage)/Σ(Sampled Current Values)

The control unit 78 calculates the estimated connection strength according to Equation (1), using the impedance calculated above. A predetermined range of acceptable reference connection strength values for good connections is stored in a storage unit 80. Since the strength data may vary with the test conditions such as the type of lead to be tested and the vibration direction of the probe 32 with respect to the lead 12, reference strength values need to be prepared for the respective test conditions to be used. The control unit 78 judges the connection quality by comparing the calculated strength value with the reference strength values stored in the storage unit 80. The judgment result is stored in the storage unit 80 and used for rejection or repair of defective products.

Figure 7:
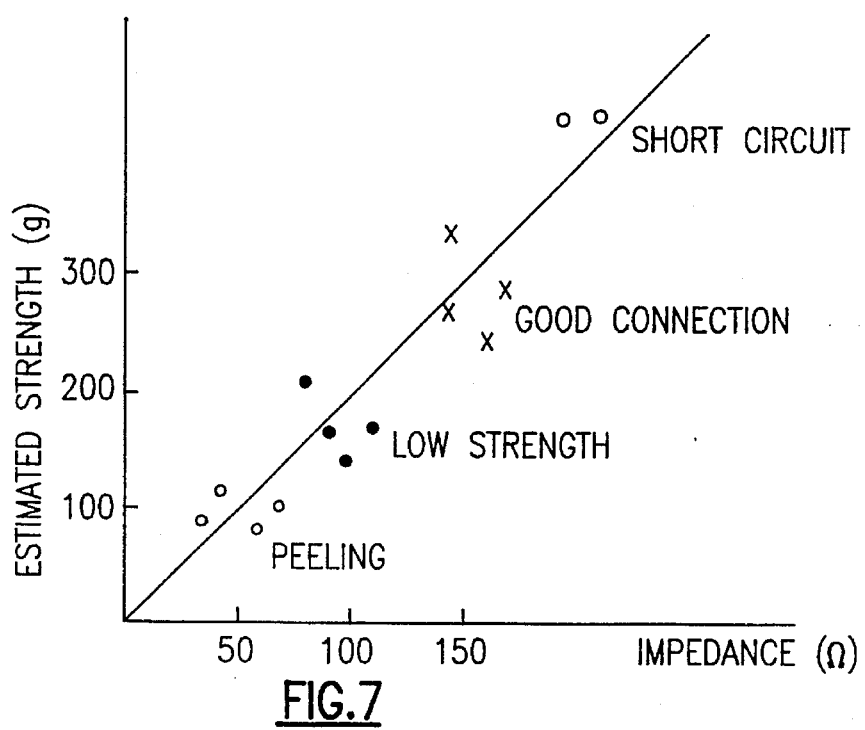
FIG. 7 is a graph showing the relationship between impedance and estimated strength.

In an experiment, a ceramic probe 11.1 mm in length, 1.6 mm in diameter, and 0.1 mm (100 microns) in tip diameter was used, and the probe vertical load was set at 50 g. The oscillation frequency and the oscillation output were 60 kHz and 1.5 V, respectively. The maximum oscillation amplitude of the probe tip under the unloaded condition (where the probe tip is not in contact with the lead surface) was ±2 microns. The oscillation amplitude of the probe tip when it landed on a lead 12 with a good solder connection was about ±0.2 micron or less. Soldered leads 12, 0.2 mm (200 microns) in width, were tested by vibrating the probe 32 in the lead width direction. The output of the oscillator 41 was applied to the piezoelectric element 38 for 20 milliseconds (oscillator ON time), and 50 samples of the rectified current were taken. Then the impedance of the piezoelectric element 38 was calculated according to Equation (2), and the distribution of estimated breaking strength values corresponding to the impedances was calculated according to Equation (1). FIG. 7 shows a measurement result of a typical case. In this manner, clear discrimination was obtained among quality grades of the connection as a function of the estimated connection strength. "Peeling" means the case where the solder joint easily separates and forms an open circuit. "Low strength" means the case where the connection strength is lower than the required level. "Short circuit" means the case where too much solder is used. It has been shown that when too much solder is used, solder bridging occurs at a probability of about 60% or more. Although, of course, the solder joints 14 exhibit a variety of distributions in accordance with its connection state, it has been confirmed that the connection strength can be estimated very accurately and nondestructively by measuring the impedance.

In the case where the oscillator ON time was set at 20 milliseconds and the data processing time was less than 10 milliseconds, the testing time per lead connection, including the probe movement time, was not more than 0.1 second. Thus the test could be performed at a very high speed.

The vertical load is not a critical factor for the present invention, and can be set arbitrarily at a proper value as long as it does not destroy the normal solder joint 14. The oscillation frequency is also not a critical factor, and can be selected from a wide range. But it is noted that too low a frequency reduces the testing speed.

Although in the above embodiment the connection quality is judged by estimating the connection strength from the impedance of the piezoelectric element 38, it is possible to judge the connection quality directly from the impedance calculated according to Equation (2) to speed up the testing. To judge the connection quality from the impedance, a predetermined range of acceptable reference impedances which have been determined for good solder joints 14, may be stored in advance in the storage unit 80 (see FIG. 6) and the measured impedance may be compared with the reference impedances stored in the storage unit 80. In this case, the testing speed can be increased because the connection strength calculation is omitted.

To further speed up the testing, the connection quality can also be judged directly from the current. In this case, a predetermined range of acceptable reference current values which have been determined from good solder joints, may be stored in advance in the storage unit 80 and the measured current may be compared with the reference current values stored in the storage unit 80. Where the current output from the rectifier circuit 74 (see FIG. 6) does not include large noise components and the signal is stable, the current can be detected by sampling the output of the rectifier circuit 74 once or a few times and calculating an accumulated value or average value. According to this method, the time for the data sampling and the calculations can be reduced to about 1/10.

Although the method of using the current is the fastest, it is likely to cause errors when the current includes noise or is unstable. Therefore, to speed up the testing, the method of using the impedance is preferable. Since the current and the impedance vary with the vertical load and the oscillator voltage, a judgment reference (threshold level) needs to be prepared for each operating condition actually used. While the method of using the connection strength calculated according to Equation (1) requires a slightly longer testing time, it has the advantage that by setting the constants a and b in advance for each operating condition, a common judgment reference can be used and the testing can be simplified.

Figure 8:
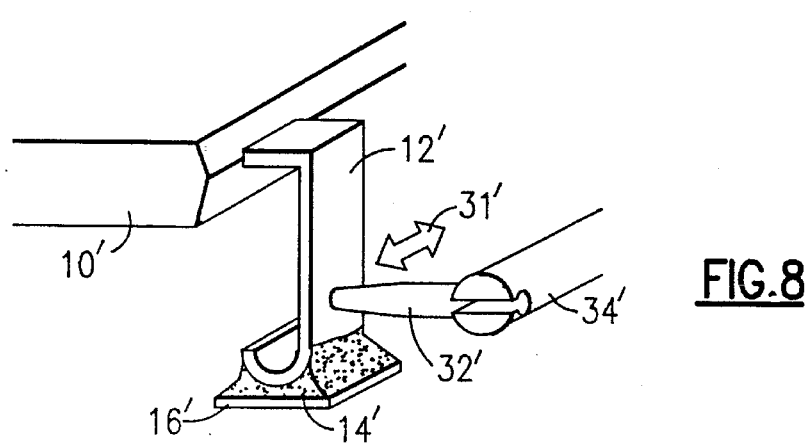
FIG. 8 is a perspective view showing a case in which the testing of the invention is applied to a J-type lead.

While in FIG. 3 the testing of the chip package 10 with gull-wing type leads 12 is taken as an example, the invention can also be applied to the testing of a chip package with so-called J-type leads. FIG. 8 shows the latter case. A chip package 10' has J-type leads 12' connected to conductors 16' by solder 14'. The probe assembly is supported in such a way that the probe 32 is oriented horizontally and its flat tip is brought into contact with the outer surface of a vertical leg portion of the J-type lead 12'. The probe 32 is vibrated in parallel with the outer surface in the width direction of the lead 12' (indicated by arrow 31'). In this case, the probe 32 is loaded toward the lead surface. The probe 32 should be in contact with the portion of the lead 12' adjacent to the solder joint 14'. It has been found that the connection quality of the J-type lead can also be judged with the above-described judgment algorithm for the gull-wing type lead.

It is to be noted that the invention is not limited to the particular embodiment described above. For example, while the above embodiment is directed to the testing of chip packages using solder as the bonding material, the present invention may be applicable to the testing of other packages using other types of conductive bonding materials as long as a shearing force causes a strain in those materials. Furthermore, the probe may be vibrated in the longitudinal direction of the lead or in an oblique direction. In those cases, of course, reference data for good connections need to be prepared in the same vibration direction.

ADVANTAGES OF THE INVENTION

As described above, according to the present invention, the shearing strain corresponding to the connection strength is generated in the lead bond portion by the probe vibration that is caused by the piezoelectric element, and the strain is measured based on the current or impedance of the piezoelectric element. Therefore, the method of the invention can detect, in a nondestructive and quantitative manner, those defects which could not be detected by the conventional visual appearance test and so on, and can greatly improve the detection rate for defective connections. While the defect detection rate of the conventional X-ray testing method and optical testing method was about 90%, that of the method of this invention is almost 100%. Furthermore, since a subtle variation in the probe vibration can be detected by direct detection of the current of the piezoelectric element, the method of the invention has high sensitivity. The testing can be performed on a realtime basis at high speed, i.e., with a testing time of not more than 0.1 second per lead. In addition, since the probe vibrates on the lead, the sole requirement for the dimensions of the probe is that the probe does not extend out from the sides of the lead. With such loose limitations on the probe dimensions, the method of this invention can easily be applied to high-density packages with many leads.

I claim:

1. A method for producing interconnect structures, comprising the steps of:

connecting leads of a first material, of electronic components to conductors of substrates, by joints of a different second material which are strained when subjected to a shearing force;

pressing the tip of a probe onto the surface of one of the leads;

vibrating the probe in parallel with the surface of the lead to cause a sheering force;

detecting a strain occurring in the joint in response to the vibration; and judging the quality of the lead connection based on the detected strain.

2. The method of claim 1, wherein the second material comprises solder.

3. The method of claim 1, wherein the vibration of the probe is generated by a piezoelectric element, and wherein the detecting step includes measuring a current flowing through the a piezoelectric element.

4. The method of claim 3, wherein the judging step includes comparing the measured current with a reference current for good lead connection.

5. The method of claim 1, wherein the detecting step includes measuring the electrical impedance of a piezoelectric element.

6. The method of claim 5, wherein the judging step includes comparing the measured impedance with a reference impedance for good lead connection.

7. The method of claim 5, wherein the detecting step includes detecting the connection strength of the lead based on the electrical impedance of the piezoelectric element, and wherein the judging step includes comparing the detected strength with a reference strength for good lead connection.

8. Apparatus for testing interconnect assemblies in which electronic components are connected by leads to conductors of substrates by joints which are strained when subjected to a shearing force, the apparatus including:

a probe assembly including a probe and a vibration element for vibrating the probe in a direction perpendicular to the axis of the probe;

means for holding an interconnect structure in a fixed position relative to the probe assembly;

means for positioning the probe assembly so that a tip of the probe is placed on a surface of the lead;

means for applying a predetermined axial load to the probe so that the tip of the probe is pressed against the surface of the lead;

means for energizing the vibration element;

means for detecting a strain caused in the joint by the vibration of the probe; and means for judging the quality of the lead connection based on the detected strain.

9. The apparatus of claim 8, wherein the detecting means includes means for measuring a current flowing through a piezoelectric element.

10. The apparatus of claim 9, wherein the judging means includes means for comparing the measured current with a reference current for good lead connection.

11. The apparatus of claim 8, wherein the detecting means includes means for measuring the electrical impedance of a piezoelectric element.

12. The apparatus of claim 11, wherein the judging means includes means for comparing the measured impedance with a reference impedance for good lead connection.

13. The apparatus of claim 11, wherein the detecting means includes means for rectifying the current flowing through a piezoelectric element, means for sampling the rectified current at predetermined times, and means for determining the electrical impedance of the piezoelectric element based on the number of the sampling times, sampled current values, and the voltage of the energizing means.

14. The apparatus of claim 12, further including means for storing reference strength data for good lead connection, wherein the detecting means includes means for detecting connection strength of the lead based on the impedance of the piezoelectric element, and wherein the judging means includes means for comparing the detected strength with the reference strength data stored in the storing means.

15. An interconnect structure comprising:

a substrate having metal contacts;

at least one electronic component on the substrate;

leads connected to the component and extending to and along the contacts;

solder joints connecting the leads to the contacts, which when subject to equal loads applied by the leads exhibit a range of strains limited by a maximum strain determined for a joint with the minimum acceptable joint size.

16. The structure of claim 15 in which the leads include J-type or gull-wing surface mounting leads.

17. The structure of claim 15 in which the leads of at least one of the components have a rectangular cross-section with two wider sides and two narrow sides and the solder joint is connected to one of the wider sides.

18. The structure of claim 15 in which the maximum of range of strain is also limited to less than that exhibited by any non-bridging joints with unacceptable cracks or inclusions.

19. A method for testing circuit boards in which an electronic component is connected by leads, the leads being connected to conductors of a substrate by joints which are strained when subjected to a shearing force, the method comprising the steps of:

pressing the tip of a probe onto the surface of the lead;

vibrating the probe in parallel with the surface of the lead;

detecting a strain occurring in the joint in response to the vibration; and judging the quality of the lead connection based on the detected strain.

20. The method of claim 1 in which the substrate comprises a circuit board substrate.

21. The apparatus of claim 8 in which the means for holding an interconnect structure comprises means for holding a circuit board.

22. The method of claim 1 in which the sheering force correlates with the product of the vertical force and the friction coefficient between the probe and lead.

* * * * *